(12) United States Patent
Costin

(10) Patent No.: US 6,350,742 B1
(45) Date of Patent: *Feb. 26, 2002

(54) COMPOSITIONS AND METHODS FOR TREATING INFECTIONS OF THE EAR

(75) Inventor: James C. Costin, Lower Gwynedd, PA (US)

(73) Assignee: Carter-Wallace, Inc., New York, NY (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/266,056

(22) Filed: Mar. 10, 1999

Related U.S. Application Data

(63) Continuation-in-part of application No. 09/151,885, filed on Sep. 11, 1998.

(51) Int. Cl.$^7$ .............................................. A61K 31/54
(52) U.S. Cl. ................. 514/222.2; 514/223.2
(58) Field of Search ............................ 514/222.2, 223.2

(56) References Cited

U.S. PATENT DOCUMENTS 3,423,408 A * 1/1969 Pfirrmann .................... 260/243
4,604,391 A * 8/1986 Pfirrmann .................... 514/222

* cited by examiner

Primary Examiner—Kevin E. Weddington
(74) Attorney, Agent, or Firm—Kevin B. Clarke

(57) ABSTRACT

The use of 4,4-methylenebis(tetrahydro-1,2,4-thiadiazine-1,2-dioxide) in treating infections of the ear.

4 Claims, No Drawings

COMPOSITIONS AND METHODS FOR TREATING INFECTIONS OF THE EAR

This application is a continuation-in-part of U.S. application Ser. No. 09/151,885 filed Sep. 11, 1998.

BACKGROUND OF THE INVENTION

This invention relates to novel antimicrobial compositions and their use. In particular, this invention relates to compositions which contain 4,4'-methylenebis (tetrahydro-1,2,4-thiadiazine)1,1,1',1',-tetraoxide and their use in treating infections of the ear, i.e. otitis media and otitis externa.

The chemical and medical literature describes a myriad of compounds that are said to be antimicrobial, i.e., capable of destroying or suppressing the growth or reproduction of microorganisms, such as bacteria. In particular, antibacterials include a large variety of naturally-occurring antibiotic, synthetic, or semi-synthetic compounds. They may be classified for example as the aminoglycosides, ansamacrolides, beta-lactams, including penicillins and cephalosporins, lincos-aminides, macrolides, nitrofurans, nucleosides, oligosaccharides, peptides and polypeptides, phenazines, polyenes, polyethers, quinolones, tetracyclines, and sulfonamides. Such antibacterials and other antimicrobials are described in Antibiotics, Chemotherapeutics, and Antibacterial Agents for Disease Control (M. Grayson, editor, 1982), and E. Gale et al., The Molecular Basis of Antibiotic Action 2d edition (1981), both incorporated by reference herein.

The mechanism of action of these antibacterials vary. However, each can be generally classified as functioning in one or more of four ways: by inhibiting cell wall synthesis or repair; by altering cell wall permeability; by inhibiting protein synthesis; or by inhibiting synthesis of nucleic acids. For example, beta-lactam antibacterials act through inhibiting the essential penicillin binding proteins in bacteria, which are responsible for cell wall synthesis. On the other hand, quinolones act by inhibiting synthesis of bacterial DNA, thus preventing the bacteria from replicating.

Not surprisingly, the pharmacological characteristics of antibacterials and other antimicrobials, and their suitability for any given clinical use, also vary considerably. For example, the classes of antimicrobials and members within a class may vary in their relative efficacy against different types of microorganisms, and their susceptibility to development of microbial resistance. These antimicrobials may also differ in their pharmacological characteristics, such as their bioavailability, and biodistribution. Accordingly, selection of an appropriate antibacterial or other antimicrobial in any given clinical situation can be a complicated analysis of many factors, including the type of organism involved, the desired method of administration, and the location of the infection to be treated.

The pharmaceutical literature is replete with attempts to develop improved antimicrobials, i.e., compounds that have a broader scope of activity, greater potency, improved pharmacology, and/or less susceptibility to resistance development. For example, one group of antimicrobials that has been developed relatively recently for clinical use is the quinolones. These compounds include, for example, nalidixic acid, difloxacin, enoxacin, fleroxacin, norfloxacin, lomefloxacin, ofloxacin, ciprofloxacin, and pefloxacin. See C. Marchbanks and M. Dudley, "New Fluoroquinolones," 7 Hospital Therapy 18 (1988); P. Shah, "Quinolones," 31 Prog. Drug Res. 243 (1987); Quinolones—Their Future in Clinical Practice, (A. Percival, editor, Royal Society of Medical Services, 1986; and M. Parry, "Pharmacology and Clinical Uses of Quinolone Antibiotics," 116 Medical Times 39 (1988).

However, many such attempts to produce improved antimicrobials have produced equivocal results. Indeed, few antimicrobials are developed that are truly clinically-acceptable in terms of their spectrum of antimicrobial activity, avoidance of microbial resistance, and pharmacology. For example, the quinolones often show reduced, effectiveness against certain clinically important pathogens, for example, gram positive bacteria and/or anaerobic bacteria. The quinolones also have limited water solubility limiting their bioavailability and suitability for parenteral dosing. They may also produce adverse side effects, such as gastrointestinal disturbance and central nervous system effects, such as convulsions. See, M. Neuman and A. Esanu, "Gaps and Perspectives of New Fluoroquinolones," 24 Drugs Exptl. Clin. Res. 385 (1988); W. Christ et al., "Specific Toxicologic Aspects of the Quinolones," 10 Rev. Infectious Diseases S141 (1988); H. Neu, "Clinical Use of the Quinolones," Lancet 1319 (1987); and "Ciprofloxacin: Panacea or Blunder Drug?," J. South Carolina Med. Assoc. 131 (March 1989).

SUMMARY OF THE INVENTION

This invention provides methods and compositions for the treatment of bacterial infection referred to as otitis media or otitis externa presenting as inflammation of the mucosal lining of the external and/or middle ear usually with exudation which compositions in addition to killing and eradicating pathogens also reduce or eliminate the ability of pathogens to acquire resistance to antibiotic drug treatment. Moreover, this invention relates to methods and compositions for the reduction or elimination of bacteria associated with otitis media and otitis externa.

Specifically, the present invention relates to the use of 4,4'-methylenebis (tetrahydro-1,2,4-thiadiazine)-1,1,1',1' tetraoxide known generically as taurolidine to eradicate or control the indigenous microbiota of the ears, namely:

Gram-positive Cocci

*Staphylococcus epidermidis*
*Staphylococcus aureus*
*Anaerobic micrococci*
*Streptococcus mitis*
undifferentiated
α and Y streptococci
*Streptococcus pneumoniae*

Gram-positive Bacilli

Lactobacillus spp.
Aerobic corne bacterium spp.

Aerobic Gram-negative Bacilli

Enterobacteriaceae
*Escherichia coli*
Enterobacter spp.
Klebsiella spp.
*Proteus mirabilis other*
Proteus spp.
*Morganella morganii*
Providencia spp.
*Pseudomonas aeruginosa*
*Alcaligenes Faecalis*

Further, the present invention relates to the use of taurolidine to prevent the development of antibiotic drug resistance in the microbiota of the ear.

Taurolidine occurs as a white to off-white powder having the molecular formula $C_7H_{16}N_4O_4S_2$ and a melting point of 154–158° C.

Taurolidine's general characteristics include acceptable stability in the solid state when stored at ambient conditions, melting with decomposition at approximately 170° C. and the following solubility in aqueous solutions and organic solvents.

| | |
|---|---|
| Water | 1% at 20° C. |
| Dilute HCl | soluble |
| Dilute NaOH | soluble |
| $CHCl_3$ | insoluble |
| EtOH | sparingly soluble |
| DMF | 1 g in 2 mL/ca.60° C. |
| Acetone | 1 g in 120 mL/Boiling |
| Ethanol | 1 g in 130 mL/Boiling |
| Methanol | 1 g in 170 mL/Boiling |
| Ethyl Acetate | 1 g in 200 mL/Boiling |

A saturated solution of taurolidine in deionized water has a pH of 7.4. The apparent partition coefficient of taurolidine between octanol and water (buffered at pH 7.2) is approximately 0.13 and would therefore not be predicted to accumulate to any significant extent in fatty tissues.

The synthesis of taurolidine is covered in a number of patents including U.S. Pat. No. 3,423,408; Switzerland No. 482,713 and United Kingdom No. 1,124,285 and is carried out in five stages:

Potassium phthalimidoethane sulphonate is prepared from taurine, phthalic anhydride, glacial acetic acid and potassium acetate;

Potassium phthalimidoethane sulphonate is then converted to phthalimidoethane sulphonylchloride by chlorination with phosphorous oxychloride;

Phthalimidoethane sulphonylchloride is reacted with ammonia to form phthalimidoethane sulphonamide;

Phthalimidoethane sulphonylchloride is reacted with hydrazine hydrate and in the subsequent hydrazinolysis to form taurinamide hydrochloride; and Taurolidine is prepared from taurinamide hydrochloride and formaldehyde.

The antimicrobial actions of taurolidine have been described in U.S. Pat. No. 3,423,408 and elsewhere in the literature. In addition, the following United States patents describe various uses for and compositions containing taurolidine: U.S. Pat. No. 4,107,305, treatment of endotoxaemia; U.S. Pat. No. 4,337,251, elimination of adhesion formation as a result of surgery; U.S. Pat. No. 4,587,268, resorbable aqueous gels; U.S. Pat. No. 4,604,391, prevention of the occurrence of osteitis or osteomyelitis; U.S. Pat. No. 4,626,536, combating toxic proteins or peptides in the blood; U.S. Pat. No. 4,772,468, treatment of bone cavities; and U.S. Pat. No. 4,882,149, directed to methods for filling congenital, surgical or traumatic defects with compositions comprising natural bone mineral having absorbed therein/thereon taurolidine.

Taurolidine has been shown to be safe and well tolerated at systemic doses exceeding 40 g/day and cumulative doses up to and exceeding 300 g.

The formulations of taurolidine generally utilized are sterile solutions containing 0.5%, 1.0%, 2.0% or 4.0% taurolidine for irrigation/lavage, wound instillation, or intravenous administration, primarily for the treatment or prevention of peritonitis, sepsis or osteitis/osteomyelitis.

It has long been the goal of the pharmaceutical industry to produce antibiotic medicinal substances that have the power to kill—or at least to arrest the growth of— many disease causing bacteria such as the *H.pylori,* streptococci, enterococci and staphylococci.

It has also been observed that the susceptibility of bacteria to various antibiotic medicines can change markedly over time, i.e., the antibiotic gentamicin was widely used for about ten years to treat staphylococcal infection until the bacteria acquired a resistance to gentamicin. The realization that infectious bacteria could become immune to all available antibiotics has raised alarm in the medical community which now cautions doctors that over prescribing antibiotics can hasten the evolution of resistant germs.

Moreover, a study by the Federal Centers for Disease Control in Atlanta, Ga., has shown that nearly 8% of all enterococci isolated in hospitals nationwide were resistant to vancomycin, the antibiotic considered to be the last line of defense against organisms impervious to other drugs. This was more than 20 times the rate of resistance to vancomycin detected only four years earlier.

Of equal concern to the medical community is the ability of a bacteria, once it has acquired an immunity to an antibiotic, to transfer such immunity to other bacterium.

Resistance to antibiotics is developed in bacterium cells in a small circle of DNA known as plasmid which is a bit of matter consisting of a double-stranded DNA that is apart from the chromosomes but carries genes for a variety of functions and can replicate itself. The genes are concerned with such functions as resistance to antibiotics. Plasmids are separate from the rest of the bacterium, and they can move quite easily from one bacterium to another. This transferability of plasmids enables resistance genes to spread rapidly even among different species of bacteria. Transfer between bacteria of plasmids is accomplished through the use of *F pili* which are fine filaments resembling flagellum which are outgrowths from the bacteria cells which normally function to propel the cell, however when the *F pili* attach to another cell, a bridge is formed which permits the plasmids to spread rapidly from one cell to another.

Antibiotics generally work by interfering with the construction of the bacterial cell wall. In the case of vancomycin-resistance, its action can be thwarted by the bacteria modifying the building blocks of their cell walls by substituting a molecule of lactic acid for one of analine. The most common plasmid that confers resistance to vancomycin has a package of nine genes that set in motion this modification. A first gene enables the bacterium to manufacture lactic acid, a second gene codes for an enzyme that can cleve the analine from the cell wall building block, the product of a third gene puts lactic acid in the anilines place. Two more genes control the previous three ensuring that they are activated only in the presence of vancomycin. The remaining genes are involved in helping the resistance package mobilized itself in different ways.

It has now been found that taurolidine in addition to its known antimicrobial, antitoxin, antibacterial and antifungal properties destroys antibiotic resistant strains of *H.pylori,* staphylococci, streptococci, enterococci and other bacterial and nosocomial infections, prevents the development of antibiotic resistance in *H.pylori,* staphylococci, enterococci and other bacterial and nosocomial infections and prevents the transfer of bacteria-to-bacteria drug resistance through genetic or other means.

Taurolidine's mechanism of action unlike that of known antibiotics is based on a chemical reaction. While not being bound by any theory, during the metabolism of taurolidine to taurinamide and ultimately taurine and water, methylol groups are liberated which chemically react with the mureins in the bacterial cell walls this results in the denaturing of the complex polysaccharide and liposaccharide components of the bacterial cell wall as well as changing the double stranded DNA of the plasmid to a denatured or single stranded DNA.

Inflammatory disease of the mucosal lining of the middle ear with exudation is one of the most common infections besetting children. Almost all children have at least one episode of otitis media with effusion and approximately one-third have repeated episodes during infancy. Although antimicrobial therapy has markedly decreased the frequency of serious suppurative complications, its unbridled use may have increased the frequency of recurrent or persistent, sterile middle ear effusions, in light of the bacteria's ability to acquire immunity to antimicrobial agents.

*Streptococcus pneumoniae* is the most common pathogen in otitis media with effusion of children or adults and is found in approximately 30% of cases. *Haemophilus influenzae* accounts for 25% of cases in infancy and for 20% of cases in older children and young adults. The isolates of *H. influenzae* are almost always noncapsulated; if capsulated and of type b, it is likely that there is an associated systemic disease such as meningitis.

*Staphylococcus epidermidis* and *Branhamella* (*Neisseria*) *catarrhalis* are frequently isolated from acute middle ear effusions, but their etiologic significance has not been clearly established.

Although pneumococcal and haemophilan rates of isolation are consistent, streptococcus pyogens appears to have geographic limitations. It is found in approximately 10% of cases in cold climates, but in only 2% of patients in warmer zones.

In infants under six weeks of age, coliform bacilli account for 5% to 20% of cases of otitis media with effusion and they may be found in older children and adults who are compromised hosts. *Staphylococcus aureus* is rare in initial attacks but becomes more prominent in recurrent otitis, especially when the tympanic membrane has been ruptured.

Tuberculous and diphtheritic otitis are rarely seen today.

In chronic otitis media, the spectrum of etiologic agents changes completely to the gram-negative bacillary genera—proteus, klebsiella, enterobacter and pseudomonas. Episodic, acute exacerbations are rather common in the course of chronic disease and are caused by pneumococci, *H. influenzae* or streptococcus pyogenes.

Pneumococci, *s. aureus* and group A streptococci, in that order, are the usual pathogens in acute mastoiditis. Haemophilus spp. rarely cause acute mastoiditis in spite of a high incidence in acute otitis media with effusion.

Acute diffuse external otitis is most commonly caused by streptococci or *staphylococcus aureus*—also the cause of furuncles in the external auditory canal. *Pseudomonas aeruginosa* or other pseudomonads are characteristically isolated from patients with chronic external otitis.

Bullous myringitis was formerly attributed to infection caused by mycoplasma pneumoniae infection; however, current opinion holds that bullous myringitis is merely one manifestation of otitis media with effusion caused by various nonmycoplasmal microorganisms.

It has now been found that taurolidine eradicates or controls the growth of microbiota indigenous to the human ear thereby eliminating or reducing the severity of incidences of otitis media with effusion and external otitis.

A particular advantage of taurolidine is its very low toxicity; thus methylol transfer activity results in the production of taurine which is found naturally in the body and is particularly non-toxic.

A further advantage of taurolidine is its stability in aqueous solution, enabling the solutions to be pre-packed and stored over relatively long periods. Furthermore, it has been shown to be non-teratogenic in mice.

According to the present invention there are provided pharmaceutical compositions comprising taurolidine with one or more carriers or excipients. The compositions may take the form of tablets, dragees, capsules, lozenges, suppositories, ampoules for injection, syrups, linctuses, ointments, lotions, pastes, solutions, aerosol sprays, etc.

The carriers or excipients in such compositions may, for example, be those conventional for such forms and may include starch, lactose, magnesium stearate, talc, gelatin, sterile water, suspending, emulsifying, dispersing, thickening or flavouring agents, ointment bases or aerosol propellants.

Topical formulations are preferred, for example, powders, ointments, sprays, gels, solutions, etc.

The compositions, and particularly the non-dosage topical forms such as powders, sprays, solutions, gels, ointments, etc., preferably contain the active substance at a concentration between 0.10 and 20.0% by weight, preferably between 0.5 and 2.0% for aqueous solutions or aerosol sprays or up to 10% for powders, gels and ointments.

The daily dose of taurolidine depends, in part, on such factors as the body weight of the subject, the extent of infection, etc. Where the compositions of the invention are in solid form, e.g. tablets or capsules, they conveniently contain 400 to 700 mg., preferably about 500 mg of taurolidine. However, oral daily dosages will generally be at least about 10 g, preferably 10 to 30 g.

The following non-limiting examples are provided to further illustrate the present invention.

EXAMPLE 1

| Tablet | |
|---|---|
| Taurolidine | 500 g |
| Amylum maydis | 50 g |
| Kollidone 25 (polyvinylpyrrolidone) | 50 g |
| Plasdon XL | 20 g |
| Magnesium stearate | 6 g |
| Distilled water | 200 g |

1000 tablets each containing 500 mg taurolidine are produced by conventional means using the above formulation.

In an alternative tablet formulation, the amylum maydis is replaced by 60 g amylum orizae.

EXAMPLE 2

| Solution | |
|---|---|
| Taurolidine | 440 g |
| Pharmaceutical gelatin | 88 g |
| Sodium chloride | 99 g |
| Sterile water to | 22 liters |

The components are dissolved in the sterile water, if necessary using gentle warming and sonication. The solution is then filled into sterile bottles, 500 ml in each.

What is claimed is:

1. A method for the eradication and control of the indigenous microbiota of the ear which comprises administering to a human or other warm blooded animal infected with such microbiota, the compound 4,4'-methylenebis(tetrahydro-1,2,4-thiadiazine-1,2-dioxide).

2. The method of claim 1 wherein said 4,4'-methylenebis(tetrahydro-1,2,4-thiadiazine-1,2-dioxide) is combined with an additional antibiotic or antibiotics.

3. The methods of claim 1 or 2 wherein said compound is administered orally.

4. The methods of claim 1 or 2 wherein said compound is administered topically.

* * * * *